United States Patent [19]

Jones et al.

[11] Patent Number: 5,069,901

[45] Date of Patent: Dec. 3, 1991

[54] PREPARATION OF A RECOMBINANT SUBUNIT VACCINE AGAINST PSEUDORABIES INFECTION

[76] Inventors: Elaine V. Jones; Mark W. Mellencamp; Timothy J. Miller, all of SmithKline Beckman Corp., Corporate Patents N-160, P.O. Box 7929, Philadelphia, Pa. 19101

[21] Appl. No.: 151,736

[22] Filed: Feb. 3, 1988

[51] Int. Cl.$^5$ .................... A61K 39/12; C12N 15/00
[52] U.S. Cl. ........................... 424/89; 435/5; 435/172.3; 435/235.1; 435/320.1; 530/826; 935/59; 935/63
[58] Field of Search .................. 424/89; 435/172.3; 935/235.5, 59, 63; 530/826

[56] References Cited

U.S. PATENT DOCUMENTS

| | | | |
|---|---|---|---|
| 4,603,112 | 7/1986 | Paoletti et al. | 435/235 |
| 4,711,850 | 12/1987 | Kit et al. | 435/235 |
| 4,810,634 | 3/1989 | Post et al. | 435/235 |

FOREIGN PATENT DOCUMENTS

87/02058  9/1987  PCT Int'l Appl.
87/00862  12/1987  PCT Int'l Appl.

OTHER PUBLICATIONS

Wiktor et al., "Protection from Rabies by a Vaccinia Virus Recombinant Containing the Rabies Glycoprotein Gene", Proc. Natl. Acad. Sci. USA, vol. 81, pp. 7194–7198, 1984.

Marchioli et al., "Evaluation of Pseudorabies Virus Glycoprotein gp 50 as a Vaccine for Aujeszky's Disease in Mice and Swine: Expression by Vaccinia Virus and Chinese Hamster Ovary Cells", J. Virol., vol. 12, pp. 3977–3982, 1987.

Petrovskis et al., "Use of λgt11 to Isolate Genes for Two Pseudorabies Virus Glycoproteins with Homology to Herpes Simplex Virus and Varicella-Zoster Virus Glycoproteins", J. Virol., vol. 60, No. 1, pp. 185–193, 1986.

Cremer et al., "Vaccinia Virus Recombinant Expressing Herpes Simplex Virus Type 1 Glycoprotein D Prevents Latent Herpes in Mice", Science, vol. 228, pp. 737–740, 1985.

Petrovskis et al., Pseudorabies Virus Protein, 9 Apr. 1987, PCT WO87-02058.

Post et al., Virus Vaccine, 12 Feb. 1987, PCT WO8-7-00862.

*Primary Examiner*—Margaret Moskowitz
*Assistant Examiner*—Abdel A. Mohamed

[57] ABSTRACT

A method of preparation of a vaccine for use in immunizing animals against pseudorabies virus (PRV) infection which comprises inactivated recombinant PRV subunit antigens. Also described is a diagnostic kit for detection of PRV infection which distinguishes vaccinated animals from naturally exposed animals.

16 Claims, 1 Drawing Sheet

PREPARATION OF A RECOMBINANT SUBUNIT VACCINE AGAINST PSEUDORABIES INFECTION

FIELD OF INVENTION

This invention relates to a method of preparation of an inactivated subunit vaccine useful for the immunization of animals against the pseudorabies virus (PRV) and the development of a diagnostic test capable of distinguishing vaccinated animals from naturally exposed animals.

BACKGROUND OF THE INVENTION

Pseudorabies (Aujeszky's disease) is a highly infectious disease of domestic animals, including swine, cattle, sheep, dogs, cats, mink and rats, caused by pseudorabies virus (PRV), a member of the herpes virus family (Roizman, et al., *Intervirology* 16:201(1981)). Swine are the primary host for this virus and piglets under five weeks of age are most susceptible. Adult pigs often become latently infected following exposure to PRV only to have the virus reactivated later in time.

The disease is characterized by severe respiratory illness, abortions, reduced litter size, decreased growth rate and an often fatal encephalitis (Gustafson, in *Diseases of Swine*, Dunn and Ledman, Eds., Iowa State Press, 1975). Current control measures include vaccination with either inactivated or attenuated PRV or test and removal procedures (See Gustafson, supra, (1975).

Modified live virus (MLV) and inactivated whole virus vaccines have been used extensively as a source to induce immunity against many diseases. Modified live virus stocks are generally produced by multiple passages in permissive or semi-permissive cell lines. One common feature of high passage virus stocks is that they are usually less virulent or attenuated.

PRV vaccines have been produced by a variety of methods. However, the MLV forms of vaccination result in the virus being maintained in the environment. Thus, complete eradication of the virus is impossible. An alternative vaccination approach would be the use of an inactivated recombinant vaccine expressing selected immunogenic PRV glycoproteins. The development of such a vaccine requires a knowledge of the organization of the PRV genome and the glycoproteins it encodes.

The PRV genome consists of a double-stranded DNA molecule with a molecular weight of approximately 90 kilo daltons (Kd) (Rubenstein and Kaplan, *Virology* 66:385(1975)). The genome is separated by inverted repeat sequences into a unique short ($U_S$) and a unique long ($U_L$) region (Stevely, *J. Virol.* 22:232(1977); Ben-Porat, et al., *Virology* 95:285(1979)). Viral glycoproteins have been shown to be encoded by genes located in both the $U_S$ and $U_L$ regions of the genome. It has been found that in at least two strains of attenuated PRV (Norden and Bartha strains; Norden Laboratories, Lincoln, Nebr.), the attenuation appears to be directly correlated with a genomic deletion. (Petrovskis, et al., *J. Virol.* 60:1166(1986)). The deletion is usually about 2-4 thousand base pairs in length and is located in the $U_S$ region of the genome. At least one protein, gI, is encoded by this deleted region.

Hampl, et al., *J. Virol.* 52:583(1984) have described five glycoproteins that are incorporated into the envelope of PRV. These include gI (130 Kd), gII a,b,c (125 Kd, 74 Kd, 58 Kd), gIII (98 Kd), gIV (98 Kd), and gV (62 Kd). Another viral encoded glycoprotein referred to as gX (98 Kd) has been shown to accumulate in the medium of infected cells (Rea, et al., *J. Virol.* 54:21(1985)). Two other viral glycoproteins have been identified: gp50 (Wathen and Wathen, *J. Virol.* 51:57(1984) and gp63 (Petrovskis, et al., *J. Virol.* 59:216(1986)). The map locations of five of the glycoproteins have been reported. The gII complex and gIII have been shown to map in the $U_L$ region between map positions 0.105–0.130 and near map position 0.40, respectively (Mettenleiter, et al., *Virology* 152:66(1986); Robbins, et al., *J. Virol.* 58:339(1986)). gX, gp50, gI, and gp63 have been mapped in the $U_S$ region of the genome. (Rea, et al., supra, (1985); Wathen and Wathen, supra, (1984); Mettenleiter, et al., *J. Virol.* 53:52(1985); Petrovskis, et al., supra, (1986)). (See FIG. 1.)

In the Norden and Bartha strains, flanking the gI deletion on the upstream side, i.e., the start of the gene, are the two glycoproteins gp50 and gp63. On the downstream side, i.e., the end of the gene, is the region of DNA involved with replication. Sera from animals exposed to natural infections contain antibody to gp50, gp63 and gI. Animals vaccinated with modified live virus do not contain antibody to gI.

Several monoclonal antibodies have been produced that neutralize PRV in vitro. Hampl, et al., supra, (1984) reported that monoclonal antibodies directed against gIII effectively neutralize the virus. Monoclonal antibodies specific for gI and gII also have virus neutralizing activity (J. Rziha, personal communication; Mettenleiter, et al., supra, (1986). Wathen and Wathen, supra, (1984), reported that monoclonal antibodies raised against gp50 have virus neutralizing activity. Additionally, it has been shown that mice passively immunized with monoclonal antibodies directed against gp50 are protected following challenge with PRV.

Various attempts have been made to develop a useful vaccine for immunization of animals against PRV infection. Use of the PRV glycoprotein, gp50, as a potential subunit vaccine candidate has been reported by Marchioli, et al., *J. Virol.* 61:3977(1987). Petrokovis, et al., Patent Cooperation Treaty (PCT) Application WO 87/02058 reports the production of subunit vaccines for PRV using one of gI, gp50 and gp63 polypeptides. Production of an attenuated PRV vaccine, comprising DNA from PRV is reported by Shih, et al., PCT Application WO 87/01287. An attenuated PRV vaccine is produced using a sequence of PRV essential for replication of the attenuated virus from which a portion of the repeat sequence has been deleted.

Modification of the live PRV by use of a temperature-sensitive PRV strain has also been reported, U.S. Pat. No. 4,514,497. The production of PRV glycoprotein genes in procaryotic and eucaryotic expression systems and their use as immunogens is described by Robbins, et al., European Patent Application 0 162 738.

Recently, numerous reports have demonstrated the utility of using vaccinia virus recombinants expressing foreign viral genes as vaccines. Successful expression and immunization have been reported with infectious vaccinia virus recombinants including those containing the genes for hepatitis B surface antigen (Smith, et al., *Nature* 302:490(1983); Paoletti, et al., *Proc. Natl. Acad. Sci. USA* 81:193(1984), influenza virus hemagglutinin (Panicali, et al., *Proc. Natl. Acad. Sci. USA* 80:5364(1983); herpes simplex glycoprotein D (Paolettl, et al., supra, (1984); Cremer, et al., *Science* 228:737(1985); rabies glycoprotein G (Wiktor, et al.,

*Proc. Natl. Acad. Sci. USA* 81:7194(1984)), vesicular stomatitis glycoprotein G (Mackett, et al., *Science* 227:433(1985), and human respiratory syncytial virus G glycoprotein (Ball, et al., *Proc. Natl. Acad. Sci, USA* 83:246(1986); Elango, et al., *Proc. Natl. Acad. Sci. USA* 83:1906(1986)).

SUMMARY OF THE INVENTION

One embodiment of the invention is a recombinant pseudorabies virus (PRV) vaccine for administration to an animal capable of inducing immunity against infection by PRV without serious side effects. Such vaccine comprises an effective amount of recombinant PRV divalent subunit antigens, gp50:63.

In another embodiment of the invention, a method of preparation of a vaccine against PRV infection is described which comprises expressing PRV subunit antigens, gp50:63 in a vaccinia virus tissue culture system; treating the recombinant virus with a chemical inactivating agent and collecting the inactivated recombinant virus and cell extract for formulation into a vaccine.

In still another embodiment of the invention, a method of immunization of animals against PRV infection is described which comprises the administration of recombinant PRV subunit antigens, gp50:63 expressed in a recombinant vaccinia virus system by an oral, intranasal, intraperitoneal, subcutaneous or intramuscular route.

In another embodiment of the invention, a recombinant vaccinia virus which expresses the PRV gp50:63 is described wherein the recombinant vaccinia and cell extract has been inactivated.

In yet another embodiment, a vaccine dosage unit for inducing immunity to infection by PRV is described which comprises 0.1 to 5.0 ml of a liquid suitable for intranasal, intramuscular, intraperitoneal, subcutaneous or oral administration to an animal, containing 1.0 to 100 µg of gp50:63.

In another embodiment of the invention is described a combination vaccine for oral, intramuscular, intraperitoneal, subcutaneous or intranasal administration capable of inducing immunity in animals to infection by PRV and one or more other pathogenic organisms or viruses without serious side effects. The combination vaccine comprises an effective amount of PRV subunit antigens, gp50:63 and effective amounts of one or more other antigens protective against infection by another pathogenic organism or virus.

In still another embodiment a diagnostic kit for the detection of PRV infection in animals comprising the recombinant PRV subunit antigen, gI is described.

Detailed Description of the Invention

The control of any infectious disease preferably includes means to both prevent and monitor the disease. In the study of PRV infection, it has become apparent that it is also of importance to prevent spread of the virus while providing immunization of the animals. To date the problem has been obtaining an effective vaccine without further introduction of the virus into the environment. The production of a vaccine which will protect animals without further introducing PRV into the environment is the subject of this invention.

In one embodiment of the invention, a method of preparation of a recombinant inactivated subunit vaccine or derivatives thereof for pseudorabies infection is set forth. The PRV subunit vaccine is constructed so as to establish an immunity in vaccinated animals that can be distinguished from animals which have been exposed to natural infection. In addition, the vaccine does not induce a latent state of PRV infection in the vaccinated animals.

A vaccine having such properties can be prepared by using the two pseudorabies glycoproteins (gp50 and gp63) as the subunit components of the vaccine as a single antigenic preparation herein identified as gp50:63.

The vaccine of the invention includes derivatives of the subunit antigen component. Such derivatives comprise additions, deletions or substitutions, which alterations do not significantly adversely affect the ability to act as a potent immunogen.

The PRV exemplified in this invention is the Indiana Funkhauser (IND-F) strain. Other PRV strains are available, for example, the Bucharest (BUK) strain and can be obtained from such sources as the National Veterinary Service Laboratory, Ames, Iowa (NVSL) or the American Type Culture Collection (ATCC), Bethesda, Md. Alternatively, useful PRV strains can be obtained from infected animals by, for example, extraction of tri-geminal ganglia, throat swab or tissue of the brain. PRV DNA is isolated from PRV by standard techniques such as described by Reed, et al., *J. Virol.* 62:266(1988).

The DNA sequences of gp50, gp63 and gI are known (Petrovskis, et al., supra, (1986); Petrovskis, et al., *J. Virol.* 60:185(1986)). This allows for a specific and detailed identification of the genes encoding these proteins. Isolation of the regions of the PRV genome encoding gp50, gp63 and gI can be carried out using standard cloning techniques as described, for example, in Maniatis, et al., *Molecular Cloning: A Laboratory Manual*, Cold Springs Harbor Laboratory, 1982. The isolated regions from the PRV genome can be cloned into, for example, vaccinia virus vectors, dihydrofolate reductase (dhfr) vectors (Marchioli, et al., supra, (1987)), and *Escherichia coli* vectors (Petrovskis, et al., supra, (1986)), yeast vectors or other gram-positive vectors, e.g., Bacillus or Streptomyces (in *Cloning Vectors*, Pouwels, Enger-Valk, Eds., 1985).

The recombinant genes so produced can be expressed in both eucaryotic and procaryotic host cells. For example, expression in procaryotic host cells can be achieved using *E. coli, B. subtilis*, Streptomyces or *S. typhimurium*, Cyanobacteria, or *S. aureus (in Cloning Vectors, supra,* (1985)). Expression in eucaryotic host cells can be carried out using mammalian cells, for example, Chinese Hamster Ovary cells (CHO), R-1610 hamster kidney cells, porcine kidney cells, swine testicular cells; yeast cells, for example, *S. cerevisiae* and Pichea; and insect cells, for example, *S. frugiperida* and Drosophila.

Expression systems in which the PRV antigen is expressed on the surface of an immunogenic particle are preferred, e.g., vaccinia virus, papova virus, adeno virus, herpes virus, parvovirus, papilloma virus and fowl or swine pox virus.

Using methods of recombinant DNA to express proteins in tissue culture using a vaccinia virus expression system, the genes for gp50 and gp63 can be incorporated as a colinear gene in vaccinia for production of the subunit vaccine. The diagnostic agent, gI, can be made using recombinant DNA techniques to express the gene product. This gI gene product can be utilized as an antigen for serological assays, such as, ELISA, radioimmune assays (RIA) and protein blotting.

In addition, a gI gene probe can be made by purifying the DNA encoding gI from the recombinant DNA clones containing the gI DNA. Gene probes or proteins encoded within the $U_s$ region of pseudorabies can, thereby, be used as a means of diagnosis for pseudorabies in naturally occurring infections versus responses due to vaccination with a subunit or modified live PRV vaccine. The genes or gene products encoded from the pseudorabies $U_s$ region between the StuI and BamHI (see FIG. 1) are the source for the diagnostic material. Attenuated vaccine strains of pseudorabies contain deletions in this region. Therefore, since gI is entirely encoded from this region, neither the gene nor gene products for gI can be found in highly attenuated strains of pseudorabies.

A diagnostic kit designed to detect gI, gI antibody or the gI DNA sequence can be used to determine whether the animal has been vaccinated or exposed to a pathogenic field strain. Because the subunit vaccine of the invention does not contain gI protein or DNA sequence it can also be used in similar assays. For example, inactivated recombinant vaccinia virus containing PRV gp50 and gp63 is not infectious and cannot initiate an immune response to PRV proteins other than pg50 and gp63 in animals vaccinated with this virus. These animals will, therefore, be negative for circulating antibodies to gI and should not contain any pseudorabies DNA (gI gene) in cells normally targeted by modified live or field strains of PRV.

Figure 1:
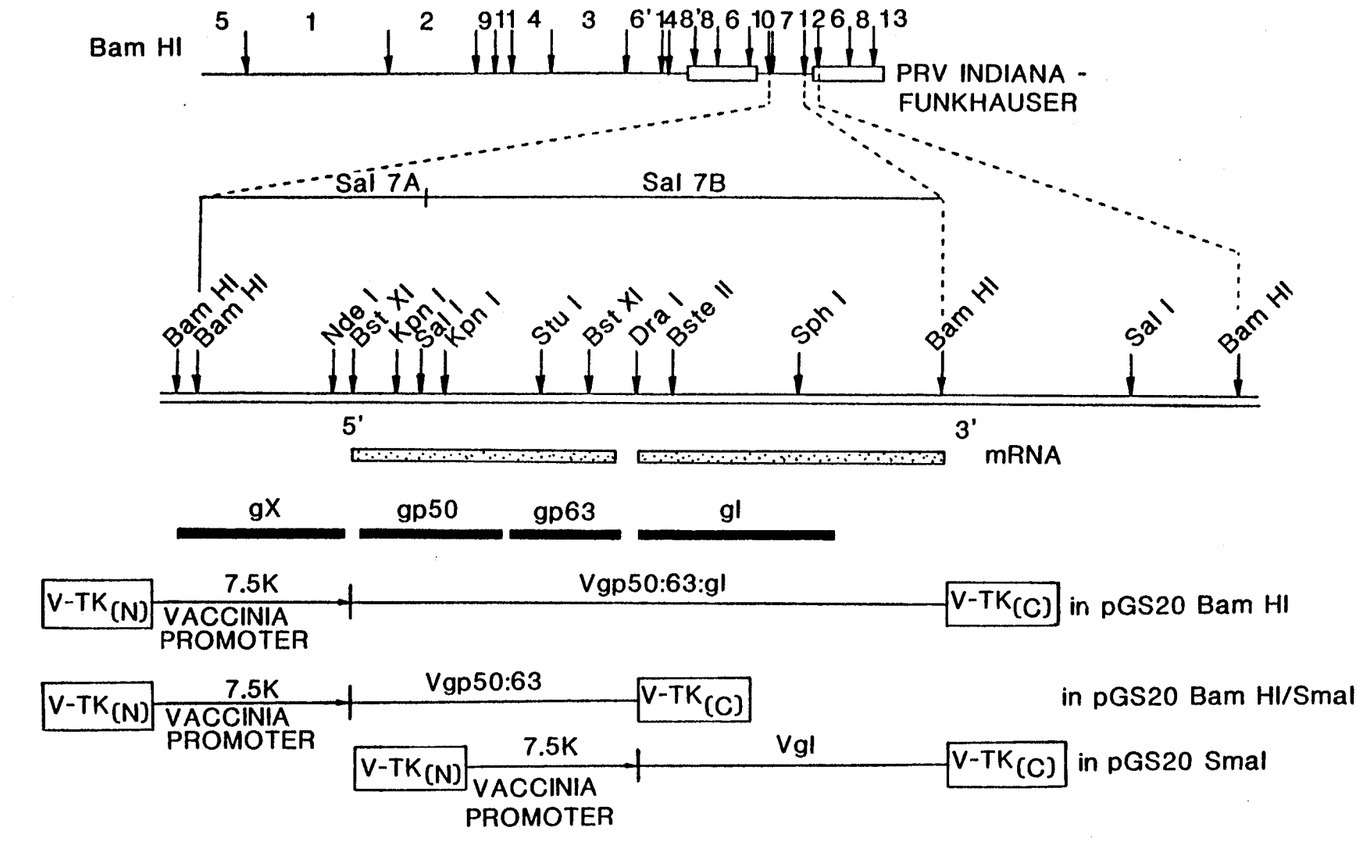
FIG. 1: Genetic map of the unique short (U$_S$) region of pseudorabies virus (PRV). The slashed bar represents mRNA transcripts as determined by S1 mapping. The thick solid bar represents the location of the genes gX, gp50, gp63 and gI. The solid lines at the bottom of the figure represent the regions of the PRV genome cloned into recombinant vaccinia vectors.

An examination of the restriction enzyme map in the gp50 coding region indicates the presence of a unique BstX I site 44 nucleotides upstream of the gp50 initiation codon (FIG. 1). Using methods such as described in the Examples, cloning vectors containing the genes for gp50, gp63 and gI can be constructed. Digestion of these cloning vectors results in fragments encoding the appropriate gene, i.e., gp50, gp63 and gI, which can then be ligated into an appropriate cloning vector, for example, ligation into BamHI/SmaI-digested pGS20, the vaccinia virus insertion vector (Mackett, et al., supra, (1984)). The important features of pGS20 which make it a useful vector to use include: the 7.5 Kd gene promoter, which has early and late vaccinia virus transcriptional regulatory signals; unique BamHI and SmaI sites located just downstream of the 7.5 Kd gene promoter for insertion of a foreign gene; and vaccinia virus thymidine kinase (TK) gene sequences flanking all of the above to direct homologous recombination into the TK locus of the vaccinia virus genome. Other vaccinia vector systems which may also be used include, for example, those described by Paoletti, et al., supra, (1984).

The ligation mixture described above can be transformed into, for example, *E. coli* DH5 (Maniatis, et al., supra, (1982)) and screened for recombinant clones.

A clone was isolated having the PRV fragment inserted in the correct orientation (p50:63:gI) and operationally linked to the 7.5 Kd gene promoter, as more completely described in the Examples. DNA sequencing indicated that the gp50 initiation codon was positioned 83 nucleotides downstream from the major mRNA start site for the wild type 7.5 Kd polypeptide.

Insertion of the PRV DNA fragment into vaccinia virus was accomplished by infecting host cells, for example, CV-1 cells (Jensen, *Proc. Natl. Acad. Sci.* 53:53(1964)) with vaccinia virus and transfecting the cells with an expression plasmid carrying the genes coding for the PRV proteins. Two days post infection, serial dilution of progeny virus were applied to monolayers of TK$^-$ cells, preferably human 143B TK$^-$ cells (gift from B. Moss, National Institute of Health), in the presence of 5-bromo-2'-deoxyuridine (BUdR) to select for TK$^-$ recombinant virus plaques. A number of TK$^-$ plaques were picked and grown in 24 well plates on TK$^-$ cells in the presence of BUdR. Aliquots of the infected cultures were filtered onto nitrocellulose and screened with a radio-labeled probe, preferably $^{32}$P, specific for the gp50 region. In this manner a number of recombinants were identified containing the 5.3 Kb PRV fragment. One of the recombinants was plaque purified three times on TK$^-$ cells in the presence of BUdR and a stock virus preparation was prepared by infecting swine testicular (ST) cells. The recombinant virus is referred to as Vgp50:63:gI.

Recombinant vaccinia virus constructs were made as described above and as more completely described in the Examples, which included the regions coding for gp50:63 (Vgp50:63) and gI (VgI). Using recombinant DNA techniques, plasmid p50:63:gI, p50:63 and pgI were constructed. The resulting recombinant vaccinia virus using p50:63 and pgI were designated Vgp50:63 and VgI, respectively.

To characterize the expression of gp50, CV-1 cells infected with the vaccinia recombinant Vgp50:63:gI were incubated with the gp50 specific monoclonal antibody MCA50-1 (gift of M. Wathen). The cells were rinsed and incubated with fluorescein conjugated goat-anti-mouse IgG. Gp50 could be detected in the cytoplasm and on the cell surface of Vgp50 infected cells, whereas no fluorescence could be detected in cells infected with nonrecombinant vaccinia virus. Gp50 expression was also examined by immunoprecipitation of $^{14}$C-glucosamine radiolabeled Vgp50 infected ST cell extracts with MCA50-1. SDS-PAGE analysis of the immunoprecipitates revealed a diffuse band with a molecular weight of 60 Kd and a sharper band with a molecular weight of 55 Kd. No proteins were detected following immunoprecipitation of vaccinia virus-infected cells. Analysis of the immunoprecipitates from PRV-infected cells showed an identical band pattern to that of Vgp50:63:gI infected cells. Thus, the gp50 synthesized by the recombinant virus infected cells appeared similar to that synthesized by PRV infected cells.

The expression of a recombinant vaccinia virus Vgp50:63 was characterized by first collecting serum from mice immunized with Vgp50:63 infected CV-1 cells. The Vgp50:63 mouse serum was then used to immunoprecipitate $^{14}$C-glucosamine labeled cell extracts infected with wild type vaccinia (Wyeth strain, New York Board of Health), and pseudorabies Bucharest (BUK) and Indiana Funkhauser (IND-F) (Mengeling, et al., *Arch. Virol.* 73:193(1982)) plus recombinant vaccinia Vgp50:63:gI, Vgp50:63, VgI. A diffuse band at about 62 Kd and spanning a region to a lower molecular weight of approximately 58 Kd was present in immunoprecipitates of PRV (BUK or IND-F) infected cells. A more confined band of 62 Kd was observed in immunoprecipitates of ST cells infected with Vgp50:63:gI or Vgp50:63.

To characterize the expression of gI, ST cells were infected with recombinant virus VgI and $^{14}$C-glucosamine cell extracts were immunoprecipitated with gI specific monoclonal antibody. A protein of 105 Kd was the major protein from immunoprecipitates from PRV or VgI infected ST cells, indicating that the recombinant is expressing a similar protein to PRV infected cells. When the BUK strain of pseudorabies virus is used, gI is absent in the BUK cells.

An inactivated subunit vaccine produced by the expression of gp50:gp63 using the vaccinia vector system can be used to successfully immunize animals against PRV infection. The vaccine produced using this method contains no intact PRV, i.e., no attenuated or inactivated PRV is present.

Using the two pseudorabies glycoproteins as the subunit component, the subunit vaccine has been demonstrated to induce a strong protective immunity when administered as an inactivated preparation containing the gp50:63 antigens in a recombinant vaccinia virus preparation in the presence of host cell extract.

Tests of the vaccine gp50:63 recombinant in mice indicate the live recombinant is least virulent and most protective when the mice are inoculated intracranially. Use of recombinant gp50:63 (Vgp50:63) preparations inactivated with a solution of binary ethylene imine (BEI) are safer and less expensive than currently available vaccines since vaccinia can easily be grown in a number of tissue culture systems, for example porcine kidney cells, swine testicular cells, CV-1 monkey cells and Vero cells (ATCC CCL81).

In a preferred practice of the invention, virus stock of recombinant gp50:63 representing a titer of 8.1 Log 10 TCID$_{50}$/ml is inactivated with BEI for 120 hours and used to inoculate pigs. Each animal received approximately one ml of the inactive virus preparation (containing 1-10 μg of PRV protein) intramuscular. At three weeks a booster was given. Oil-lecithin was used as the adjuvant. Other adjuvants may be used, for example, Quil A ™, alhydrogel or mineral oil. A group of animals were also administered commercially available vaccines, PR-Vac (modified live virus) and PR-Vac (killed) (Norden Laboratories, Lincoln, Nebr.), using normal vaccine dosages recommended by the manufacturer.

The most significant results are shown in Table 1. Recombinant gp50:63 after two doses induced very high levels of virus neutralizing antibody, whereas recombinant gp50 (contains no gp63) showed no seroconversion and no protection against disease. In addition, the same level of protection against virulent challenge was afforded by the recombinant gp50:63 compared to conventional vaccines. Gp50:63 expresses less gp50 and gp63 than produced in wild type infections. However, recombinant gp50:63 produced a very high antibody response. These results indicate that under optimum conditions of dose and adjuvant the recombinant gp50:63 would be expected to stimulate an even stronger response than the data reported in Table 1.

TABLE 1

Serologic Response of Pigs to Vaccination With PRVac, PRVac-Killed or Recombinant PRV Vaccines

| Vaccine | Pig No | VN Antibody Titer at Weeks Postvaccination | | | | | | | |
|---|---|---|---|---|---|---|---|---|---|
| | | 0$^a$ | 1 | 2 | 3$^b$ | 4 | 5 | 6$^c$ | 7 | 8 |
| PRVac-Killed | 418 | 0 | 4 | 32 | 32 | 32 | 64 | 16 | 64 | 256 |
| Serial #63 | 419 | 0 | 16 | 32 | 32 | 32 | 32 | 32 | 256 | 128 |
| | 401 | 0 | 4 | 16 | 8 | 16 | 8 | 8 | 128 | 256 |
| | 413 | 0 | 4 | 8 | 8 | 16 | 16 | 32 | 256 | 256 |
| | 409 | 0 | 0 | 8 | 32 | 16 | 8 | 8 | 256 | 128 |
| Geometric Mean | | 0 | 4 | 16 | 18 | 21 | 18 | 16 | 169 | 144 |
| PRVac | 410 | 0 | 8 | 8 | 16 | 8 | 8 | 16 | 256 | 256 |
| Serial #160C | 422 | 0 | 4 | 8 | 16 | 8 | 16 | 8 | 128 | 512 |
| | 404 | 0 | 4 | 16 | 16 | 8 | 8 | 8 | 128 | 128 |
| | 416 | 0 | 4 | 16 | 16 | 16 | 16 | 16 | 128 | 64 |
| | 417 | 0 | 0 | 32 | 16 | 16 | 16 | 32 | 64 | 32 |
| Geometric Mean | | 0 | 3 | 14 | 11 | 12 | 14 | 12.8 | 128 | 128 |
| Divalent | 420 | 0 | 0 | Died | | | | | | |
| Recombinant | 425 | 0 | 4 | 4 | 8 | 64 | 128 | 128 | 4096 | 2048 |
| (Gp50:63) | 414 | 0 | 0 | 4 | 8 | 64 | 32 | 64 | 64 | 512 |
| | 423 | 0 | 0 | 8 | 8 | 64 | 64 | 128 | 256 | 256 |
| | 407 | 0 | 0 | 4 | 8 | 128 | 128 | 128 | 256 | 512 |
| Geometric Mean | | 0 | 0 | 5 | 8 | 76 | 76 | 108 | 362 | 609 |
| Controls | 402 | 0 | 0 | 0 | 0 | 0 | 0 | 0 | 0 | 32 |
| | 412 | 0 | 0 | 0 | 0 | 0 | 0 | 0 | 0 | Died |
| | 421 | 0 | 0 | 0 | 0 | 0 | 0 | 0 | 0 | Died |
| | 411 | 0 | 0 | 0 | 0 | 0 | 0 | 0 | 0 | 16 |
| | 406 | 0 | 0 | 0 | 0 | 0 | 0 | 0 | 0 | Died |
| Geometric Mean | | 0 | 0 | 0 | 0 | 0 | 0 | 0 | 0 | 23 |

$^a$Animals were inoculated intramuscularly with 1 ml of recombinant gp50:63 adjuvanted with 5% lecithin in mineral oil (1 ml). PRvac is modified live and PRvac-killed is adjuvanted with alhydragel.
$^b$Animals receiving the recombinant gp50:63 were given a second inoculation at 3 weeks.
$^c$Animals were challenged with 3-4 TCID$_{50}$ Log$_{10}$ virulent PRV virus (IND-F) (2208) at week 6.

Table 1 shows the virus neutralization (VN) antibody titers from pigs vaccinated with various vaccine preparations. Animals were given inoculations containing 5% lecithin in mineral oil as the adjuvant with inactivated tissue culture extract from vaccinia infected cells or the licensed PRV vaccines (modified live) or (killed) distributed by Norden Laboratories. The inoculations were given intramuscularly (IM) in the neck and at 3 weeks a booster was given (PRV modified live was not given a booster). At 6 weeks post vaccination the pigs were challenged with a virulent form of pseudorabies virus. As Table 1 indicates, the VN titers of the divalent products were almost 10 times higher than the average titer seen for the licensed products.

Using the methods of the invention, a combination vaccine can also be produced. For example, the recombinant PRV vaccine can be prepared in combination with other inactivated vaccines or multiple bacterins. Bacterins which can be used include *Pasteurella multocida* (type A and D), *Hemophilus pleuropneumoniae* (strain 1,5,7), *Bordetella bronchiseptica* and *Erysipelothrix rhusiopathiae*. Methods of preparation for these bacterins are described in the Examples.

The results in Table 2 show the recombinant PRV subunit vaccine produced in vaccinia had the highest titer of any combination vaccine and compared favorably with the results for PRVac killed vaccine administered alone. A chemically extracted pseudorabies subunit vaccine preparation (SUVA), described more fully in the Examples, showed no seroconversion and afforded little protection. Thus, in combination with bacterins the recombinant vaccinia inactivated preparation (gp50:gp63) performed best.

virulent virus should experience little or no weight loss. A 5-10% weight gain over a period of 14 days after challenge is desirable.

A further aspect of this invention is the preparation and use of combination vaccines consisting of vaccinal amounts of PRV subunit antigens or derivatives thereof and one or more known animal viruses. For example, combination vaccines can be prepared consisting of the PRV subunit antigen component and one or more pathogenic components of the problematic swine infectious viruses, e.g., transmissible gastroenteritis virus (TGEV), porcine parvovirus, swine influenza virus, and *mycoplasma pneumonia*.

The preparation and use of such combination vaccines is carried out according to procedures as described herein or within the knowledge of those skilled in the art of vaccine production and use.

In an additional embodiment of the invention, a diagnostic agent is incorporated into a diagnostic kit for use

TABLE 2

Serologic Response of Pigs to Vaccination with PRVac-Killed, SUVA or Recombinant PRV Combination Vaccines

| | Vaccine | No of Animals | Geometric Mean VN Antibody Titer of Weeks Post-Vaccination | | | | | | | | | Percent Protection |
|---|---|---|---|---|---|---|---|---|---|---|---|---|
| | | | $0^a$ | 1 | 2 | $3^a$ | 4 | 5 | $6^b$ | 7 | 8 | |
| 1) | PRvac-Killed + Vaccinia-Killed | 10 | — | — | — | 0 | 1 | 1 | 0 | 6 | 152 | 80 |
| 2) | PRvac-Killed | 5 | 0 | 0 | 0 | 0 | 5 | 9 | 12 | 27 | 181 | 80 |
| 3) | PRvac-Killed Combination | 5 | 0 | 0 | 0 | 0 | 1 | 2 | 1 | 21 | 128 | 80 |
| 4) | SUVA Combination | 10 | 0 | 0 | 0 | 0 | 0 | 0 | 0 | 0 | 37 | 50 |
| 5) | Vaccinia gp50:63 Combination | 7 | 0 | 0 | 1 | 1 | 7 | 9 | 7 | 7 | 144 | 86 |
| 6. | Non Vaccinated | 10 | 0 | 0 | 0 | 0 | 0 | 0 | 0 | 0 | 45 | 40 |

Pseudorabies VN antibody titers for combination vaccines. The vaccine preparations include:
1) Pseudorabies killed vaccine (PRVac killed, Norden Laboratories) combined 1:1 with non-recombinant wild type (Wyeth) vaccinia; adjuvanted with 5% lecithin and mineral oil.
2) Conventional PRVac killed.
3) PRVAC killed mixed with a combination bacterin described in Examples. 2 ml of PRVac killed was mixed with 2 ml of bacterin preparation.
4) 2 ml of the bacterin combination mixed with 2 ml of subunit vaccine antigen (SUVA) see Examples).
5) 0.7 ml of the inactivated recombinant vaccinia gp50:63 mixed with 2 ml of the combination bacterin.
$^a$Animals were given primary inoculations intramuscularly. Second inoculation were given at 3 weeks.
$^b$Animals were challenged at the end of 6 weeks with 3-4 $TCID_{50}$ ($Log_{10}$) of virulent pseudorabies virus.

The recombinant vaccine of the present invention can be administered to the animal to directly protect the animal from PRV infection. The dosage should be safe, i.e., does not cause serious side effects nor introduce new pathogens to the environment. The formulation of the vaccine involves performing a minimal immunizing dose (MID) and optimal adjuvant study (OAS) (in the case of inactivated preparations). The volume of the minimal dose should be kept as small as possible without a concentration step. Therefore, for a biological vaccine product, the biosynthesis in cell culture should be at the highest possible level.

The administration of the vaccine is important and it can be given by several routes: intramuscularly, (IM); intranasally (IN); Orally (O); intraperitoneally (IP); or subcutaneously (SC). The intramuscular route for adjuvanted vaccine is the preferred route and a typical dose would be approximately 1-100 μg and preferably 5 μg of PRV gp50:63 in a volume of 0.5-5 ml, preferably 1 ml.

The vaccine preferably induces an immunity with a single dose over a period of 3-4 weeks. Vaccinated animals that have been challenged with virulent virus should experience a short and low febrile response and virus shedding should be reduced compared to non-vaccinated animals. Vaccinated animals challenged with in monitoring and diagnosing the presence of PRV in an animal population and distinguishing vaccinated animals from naturally exposed animals. The diagnostic kit is designed to contain sufficient reagents and materials to perform a panel of tests.

The PRV glycoprotein, gI, was targeted as the candidate for a diagnostic antigen because it is deleted in highly attenuated virus PRV preparations. Animals vaccinated with highly attenuated virus PRV are seronegative for gI. Animals exposed to natural infection have been found to be seropositive to gI.

Using the methods of the instant invention, high levels of gI protein for use as a diagnostic antigen can be produced through recombinant DNA expression.

A variety of cloning and expression systems can be used to express the gI diagnostic antigen. For example, *E. coli* vectors pAS1 or pUC8 (in *Cloning Vectors*, supra, (1985)) can be used to express gI or derivatives of gI using *E. coli* host systems. Alternatively, gI genes can be cloned into Streptomyces vectors and expressed using Streptomyces host cell systems (Gray, et al., *Gene* 32:21(1984)).

In a preferred practice of the invention, a single highly purified recombinant vaccinia virus protein was isolated from the region of the genome encoding the gI protein. This gI gene was transferred into vaccinia using standard protocols (Mackett, et al., *J. Virol.* 49:857(1983)). To determine if this recombinant was indeed making gI (105 Kd), ST cells infected with gI recombinants were immunoprecipitated with a monoclonal antibody to gI. Only one band of 105 Kd was precipitated from the gI recombinant infected cells and from wild type Funkhauser (Indiana-Funkhauser strain of PRV (PRV-Ind-FH); (Scherba, et al., *J. Am. Vet. Med. Assoc.* 173:1490(1978)) PRV infected ST cells. A similar band was not precipitated from Bucharest (BUK) modified live virus infected cells. Therefore, the gI recombinants synthesize a 105 Kd protein identical in size as that made by wild type infections indicating that recombinant gI is expressing the correct protein.

Additional evidence of biologically active gI being produced by the recombinant gI was seen in the results of the mouse virulence tests (Table 3). Normally, when genes are inserted into the vaccinia thymidine kinase gene, the recombinant virus is significantly reduced in virulence when injected into mouse brain (compare Vgp50:63 with wild type vaccinia). However, when vaccinia recombinants containing gI are inoculated intracranially the virulence is not lowered, but is actually increased slightly (compare Vgp50:63:gI, VgI with wild type vaccinia). Furthermore, release of virus from infected cells can be restored from attenuated PRV (Bartha strain) when the $U_s$ region (specifically gI) of pseudorabies is used in marker rescue experiments (Mettenleiter, et al., *J. Virol.* 61:2764(1987). These results, as well as information on the specific gI deletions in attenuated modified live virus PRV indicate that gI is involved with the virulence of PRV.

TABLE 3

Survival of mice given IC inoculations before and after challenge.

| Inoculation | Log 10 $TCID_{50}$ | % Survival Pre Challenge | $LD_{50}$ Per Dose | % Survival Post Challenge | $PD_{50}$ Per Dose |
|---|---|---|---|---|---|
| Wyeth Vaccinia | 6.1 | 0 | 4.9 | 0 | ND |
| | 5.1 | 40 | | 0 | |
| | 4.1 | 100 | | 0 | |
| | 3.1 | 100 | | 0 | |
| Vgp50-63 | 5.8 | 100 | | 100 | <2.8 |
| | 4.8 | 100 | >5.8 | 100 | |
| | 3.8 | 100 | | 100 | |
| | 2.8 | 100 | | 100 | |
| Vgp50-63-gI | 6.1 | 0 | | 0 | ND |
| | 5.1 | 0 | <3.1 | 0 | |
| | 4.1 | 20 | | 0 | |
| | 3.1 | 40 | | 0 | |
| VgI | 5.7 | 0 | | 0 | ND |
| | 4.7 | 40 | 4.4 | 0 | |
| | 3.7 | 80 | | 0 | |
| | 2.7 | 100 | | 0 | |

Mice were inoculated with 0.03 ml intracranially and monitored for 2 weeks. Survivors were challenged (IP) with approximately 30 $LD_{50}$ of wild type Funkhauser (2208).
ND Not Determined In the preferred practice of the invention, the recombinant gI protein can be used as a primary antigen in place of whole virus for a competitive ELISA diagnostic kit. The preferred method for carrying out the competitive ELISA is described in detail in the Examples.

A diagnostic kit using a gene probe which monitors gI gene deletion is also described. Using the gene probe method, as more fully described in the Examples, tissue samples from animals can be analyzed to determine exposure to the virus or vaccination status.

EXAMPLES

The examples which follow are illustrative and are not limiting of the invention. All enzymes were used according to the manufacturer's recommendation. Standard cloning procedures were as described by Maniatis, et al., *Molecular Cloning, A Laboratory Manual,* Cold Springs Harbor Laboratory, 1982.

EXAMPLE 1:

Virus Purification and DNA Isolation

I. DNA Isolation

Vaccinia virus DNA was extracted from purified vaccinia virus substantially as previously described (Garon, et al., *Proc. Natl. Acad. Sci. USA* 75:4863(1978)). For purification of PRV, swine testicular (ST) cells (Norden Laboratories, Lincoln, Nebr.) were infected at a multiplicity of 5 plaque forming units (PFU) per cell and 16 hours later the medium was collected and concentrated using a laboratory ultrafiltration apparatus. The concentrated virus was layered over a 5 ml 30% sucrose cushion in TBS (100 mM Tris (Sigma Chemical, St. Louis, Mo.), pH 7.2, 150 mM NaCl) and centrifuged at 11,000 rpm for 45 minutes at 4° C. The virus band at the interface was collected, diluted in TBS, and pelleted by centrifugation at 50,000 rpm for 30 minutes at 4° C. The virus pellet was resuspended in TBS, layered over a 30% glycerol-50% tartrate gradient in TBS and centrifuged at 40,000 rpm for 3 hours at 4° C. The virus band was collected, diluted 3-fold with TBS, and pelleted as above. The virus was suspended in TBS and stored at −70° C.

DNA was extracted by suspending the purified virus in protease K buffer (50 mM Tris-Hcl, pH 7.5, 1% SDS, 10 mM EDTA, 750 μg/ml protease K) and incubating at 37° C. for 2 hours. The sample was then incubated at 65° C. for 5 minutes and extracted with an equal volume of phenol:chloroform:isoamyl alcohol (25:25:1). The DNA was precipitated by the addition of sodium acetate to 0.3M and 2 volumes of ethanol.

II. Cloning of PRV Restriction Fragments

PRV DNA was digested with the restriction enzyme BamHI (New England Biolabs, Beverly, Mass.) and the fragments were resolved on a 0.6% low melting point agarose gel. The BamHI restriction fragment 7 (approximately 6.8 Kb) containing the gp50:63 coding region was excised from the gel and ligated into the plasmid pBR322 (Sutcliffe, *Nucleic Acids Res.* 5:2721(1978)) using the low melting point agarose cloning procedure described by Crouse, et al. (1983). The resulting plasmid (pBAM7) was digested with Sal I and BamHI cleaving the BamHI fragment 7 into two pieces designated Sal 7A (4.8 Kb) and Sal 7B (2.0 Kb). These fragments, Sal 7A and Sal 7B, were subcloned into pBR325 (in *Cloning Vectors*, Pouwels, Enger. Valk. Eds., 1985) using standard cloning procedures to generate the recombinant plasmids pSal 7A and pSal 7B.

III. Isolation of Recombinant Vaccinia Virus

CV-1 cells (Jensen, *Proc. Natl. Acad. Sci. USA* 53:53(1964)) infected with the Wyeth strain of vaccinia virus (Craigie, *Brit. J. Exp. Path.* 13:259(1932)) were transfected with calcium phosphate precipitated plasmid DNA as described (Mackett, et al., supra, (1984)). Thymidine kinase negative (TK$^-$) recombinants were selected by plaque assay on human 143 TK$^-$ cells (gift from B. Moss, National Institutes of Health) grown in the presence of 5-bromo-2'-deoxyuridine (Sigma Chemical Co., St. Louis, Mo.) (BUdR) at 25 µg/ml. Plaques were picked and used to infect human 143 TK$^-$ cells growing in 24 well culture plates. Forty-eight hours after infection, aliquots of infected cells were filtered onto nitrocellulose filter paper and hybridized with a $^{32}$P-labeled probe specific for the gp50:63 region using standard techniques (Maniatis, et al., supra, (1982)). Viruses screened positive for the PRV sequence were plaque-purified twice on human 143 TK$^-$ cells and amplified by infection of CV-1 or ST cells.

The plasmid pSAL7B was digested with the restriction enzyme BstX I and blunt-ended using *E. coli* T4 DNA polymerase Klenow fragment. BamHI linkers were ligated to the DNA which introduced a convenient restriction enzyme site for insertion/excision into the vaccinia pGS20 plasmid (FIG. 1). A second digestion with Sal I liberated a PRV fragment of about 540 bp. The plasmid pSAL7A was double-digested with BamHI and Sal I and the 4.8 Kb PRV 7A fragment was isolated. This fragment contains the gp50 coding sequence downstream from the Sal I site plus an additional 4.1 Kb (encoding gp63 and gI) of PRV sequence. The two fragments were ligated into BamHI-digested pGS20, the vaccinia virus insertion vector (Mackett, et al., supra, (1984)).

The ligation mixture described above was transformed in *E. coli* DH5 and screened for recombinant clones. A clone was isolated that had the PRV fragment inserted in the correct orientation (p50:63:gI) with respect to the 7.5 Kd gene promoter. Insertion of the PRV DNA fragment into vaccinia virus was accomplished by infecting CV-1 cells with vaccinia virus and transfecting the cells with pV50:63:gI. Two days post infection serial dilution of progeny virus were absorbed to monolayers of 143B TK$^-$ cells in the presence of BUdR to select for TK$^-$ recombinant virus plaques. A number of TK$^-$ plaques were picked and grown in 24 well plates on TK$^-$ cells in the presence of BUdR. Aliquots of the infected cultures were filtered onto nitrocellulose and screened with a $^{32}$P labeled probe specific for the gp50 region. In this manner a number of recombinants were identified containing the 5.3 Kb pair PRV fragment. One of the recombinants was plaque purified three times on TK$^-$ cells in the presence of BUdR and a stock virus preparation was prepared by infecting ST cells. The recombinant virus is referred to as Vgp50:63:gI.

Two additional recombinant vaccinia virus constructs were made which included the regions coding for gp50:63 (Vgp50:63) and gI (VgI). Plasmid p50:63:gI was digested with BamHI and DraI to liberate a 2.4 Kb fragment (gp50:63 coding region, FIG. 1) and a 2.8 Kb fragment (gI coding region, FIG. 1). The 2.4 KB fragment was directionally cloned into the BamHI to Sma I site of pGS20 to produce the plasmid p50:63. The 2.8 KB fragment was blunt ended by incubation with Klenow fragment DNA polymerase and deoxynucleotide triphosphate (dNTP) and inserted into the SmaI site of pGS20 (FIG. 1). Clones containing recombinant plasmids in the proper orientation were isolated and designated pgI. The resulting recombinant vaccinia virus engineered using plasmids p50:63 and pgI were designated Vgp50:63 and VgI, respectively.

EXAMPLE 2:

Characterization and Analysis

I. Indirect Immunofluorescence Assay

CV-1 cells were grown to confluency in Lab-tex chamber slides (Lab Tex, Naperville, Ill.). The cells were infected with approximately 5 PFU of virus and incubated at 37° C. for 6 hours. For visualization of cytoplasmic fluorescence, the cells were rinsed in phosphate buffered saline (PBS) and fixed in cold acetone. For visualization of membrane fluorescence the acetone fixation step was eliminated and the cells were heated at 65° C. for 2 hours. The cells were incubated with a 1:50 dilution of ascites fluid in PBS for 30 minutes at 37° C. followed by three rinses of 5 minutes each in PBS. Fluorescein conjugated goat-anti-mouse IgG antiserum (Cappel Laboratories, Cochranville, Pa.) at a 1:50 dilution in PBS was added. After 30 minutes at 37° C. the cells were rinsed as above, dried, and fluorescent patterns were observed.

II. Immunoprecipitation and Polyacrylamide Electrophoresis

ST cells (Norden Laboratories, Lincoln, Nebr.) grown in 60 mm dishes were infected with either vaccinia virus, Vgp50:63:gI, or PRV at a multiplicity of 5 PFU/cell. After a one hour adsorption period, the inoculum was removed and replaced with 2 ml of fresh minimum essential medium (MEM) containing 5 µCi/ml [$^{14}$C] glucosamine (Amersham Corp., Arlington Heights, Ill.) and 2% dialyzed fetal calf serum. After 16 hours at 37° C. the cells were harvested by washing twice and then scraping into PBS. The cells were pelleted by centrifugation at 1000 g for 5 minutes and resuspended in 1 ml of RIPA (1% triton X-100, 1% deoxycholate, 0.1% SDS, 0.15M NaCl, 0.01M Tris-HCl, pH 7.2). Following a brief sonication the disrupted cells were clarified by centrifugation at 12,000 g for 10 minutes.

Immunoprecipitation with mouse antibodies was performed essentially as described by Kessler, *J. Immunol.* 119:1617 (1975). Briefly, 50–100 µl volumes of radiolabeled cell extracts were preadsorbed with 100 µl of formalin-treated *Staphylococcus aureus* Cowan strain (*S. aureus*) (Kessler, *J. Immunol.* 119:1617(1975)) for 1 hour at 4° C. The cells were removed by centrifuging for 2 minutes in an Eppendorf centrifuge and 10 µl of ascites fluid was added to the clarified extracts for 1 hour on ice. 100 µl of *S. aureus* was added for 1 hour on ice and the cells pelleted as above. The immunoprecipitates were washed three times with RIPA and resuspended in 60 µl of electrophoresis sample buffer, (2% SDS, 0.2M dithiothreitol, 10% glycerol, 0.2% bromophenol blue, 63 mM Tris-HCl, pH 6.8) boiled for 5 minutes, and centrifuged in an Eppendorf centrifuge. An aliquot of the supernatant was analyzed on 10% SDS-polyacrylamide gels using the method of Laemmli, *Nature* 227:680(1970). [$^{14}$C] radiolabeled molecular weight standards (Amersham Corp., Arlington Heights, Ill.) were coelectrophoresed on each gel. After electrophoresis gels were fixed, fluorographed, dried and exposed to Kodax X-Omat AR film (Kodak, Rochester, N.Y.) at −70° C. The monoclonal antibody specific for gp50 (MCA 50-1) was a generous gift of M. W. Wathen. The characteristics of this monoclonal antibody have been described previously (Wathen, et al., *Virus Research* 4:19(1985)). The monoclonal antibody for gI was a generous gift of H. Rziha.

EXAMPLE 3:

Localization of the gp50:63 Colinear Coding Region

I. S1 Nuclease Mapping

A unique Sal I site located within the coding region of the gp50 and gp63 genes served as a reference point for mapping the 5' and 3' termini of the gp50 and gp63 transcript according to the procedure of Berk and Sharp, supra, (1977). The DNA probe used for mapping the 5' terminus was end-labeled at the Sal I site with T4 polynucleotide kinase (P-L Biochemicals, Milwaukee, Wis.) and <3000 μCi/mmole $^{32}$P-dATP ([γ-$^{32}$P-deoxyadinosine triphosphate], Amersham Corp., Arlington Heights, Ill.). The labeled fragment was digested with BstX I (restriction enzymes obtained from New England Biolabs, Beverly, Mass.) and the appropriate fragment was isolated by electrophoresis through a 1.5% agarose gel. The 3' terminus was mapped using a restriction fragment end-labeled at the Sal site with the Klenow fragment of *E. coli* DNA polymerase and α$^{32}$P-dATP. The DNA was digested with BstE II and the appropriate labeled fragment isolated as above.

A unique BstE II site located within the coding region of gI (Petrovskis, et al., supra, (1986)) (FIG. I) allowed for a reference point for mapping the 5' end of the gI mRNA. The DNA 5' probe was made by digesting with BstE II and end-labeling with T4 polynucleotide in the presence of γ$^{32}$P-ATP. The labeled probe was then digested with Stu II and the 5' probe was isolated by electrophoresis through a 1.5% agarose gel. The 3' terminus probe for gI was made by end-labeling the BamHI site using Klenow fragment DNA polymerase and a α$^{32}$P-GTP ([α-$^{32}$P-guanidine triphosphate], New England Biolabs). A second Sal I site in the BamHI fragment 12 (FIG. I) was then used to generate a 1.7 Kb probe which was isolated as described above.

Poly A+ RNA from PRV infected (8 hr.) and control ST cells was isolated by guanidine isothiocyanate extraction (Chirgwin, et al., *Biochemistry* 18:5294(1979)) and oligo dT cellulose chromatography (Aviv and Leder, *Proc. Natl. Acad. Sci. USA* 69:1408(1972)). One pmole of radiolabeled probe was denatured in 80 μl of 98% formamide containing 2 μl of 0.5M EDTA by heating at 80° C. for 10 minutes. Following denaturation, 3 μg of poly A+ RNA in 20 μl of 200 mM Pipes (pH 6.4, 2.0M NaCl, 5 mM EDTA) was added and the mixture was incubated at 65° C. for 16 hours. The tubes were placed in an ice bath and 450 μl of ice cold S1 nuclease buffer (0.28M NaCl, 0.05M sodium acetate, pH 4.6, 4.5 mM ZnSO$_4$) was added. Fifteen units of S1 nuclease were added and the samples incubated at 30° C. for 2 hours. The samples were extracted with phenol:chloroform and precipitated by the addition of 2 volumes of ethanol. For the 5' terminus mapping, the samples were fractionated on a 5% polyacrylamide-urea sequencing gel. The 3' terminus samples were separated on a 1.0% alkaline agarose gel prepared as described by McDonnel, et al., *J. Mol. Biol.* 110:119(1977)).

These mapping experiments demonstrate two mRNA transcripts. The gp50:gp63 is a colinear mRNA coding region beginning 0.56 Kb 5' of the Sal I site and ending 1.8 Kb 3' of the Sal I site. The gI mRNA transcript begins 0.4 Kb 5' of the BstE II site and ends 0.2 Kb 3' of the BamHI site (FIG. I).

II. Nucleotide Sequence Analysis

DNA fragments generated by restriction endonuclease digestion or Bal 31 deletion were subcloned into M13 vectors for sequencing by the dideoxynucleotide chain termination method (Sanger, et al., *Proc. Natl. Acad. Sci. USA* 74:5463(1977); Messing, *Methods Enzymol.* 101:20(1983)) with $^{35}$S-labeled dATP (Biggin, et al., *Proc. Natl. Acad. Sci. USA* 80:3963(1983). The sequencing gels were run as described by Reed, et al., *Biotechniques* 4:306(1986). Some fragments were also sequenced by the chemical method of Maxam and Gilbert, *Methods Enzymol.* 65:499(1980). The fragments were 5' end-labeled using T4 polynucleotide kinase and γ$^{32}$P-dATP or 3' end-labeled using the Klenow fragment of *E. coli* DNA polymerase 1 and the appropriate α$^{32}$P labeled dNTP. The sequence of both strands of DNA was determined.

Results indicated a translation initiation ATG codon located between 16–19 nucleotides 3' of the transcriptional start site defined by the S1 mapping experiment. An open reading frame of 1206 nucleotides exists encoding 402 amino acids. The gp50 sequence determined here for the Funkhauser strain of PRV (Shuba, et al., *J. Am. Vet. Med. Assoc.* 173:1490(1978)) is nearly identical to that reported for the Rice strain (Petrovskis, et al., supra, (1986)). A single base difference occurs at position 468; however, this does not result in an amino acid change.

EXAMPLE 4:

Isolation of a Recombinant Vaccinia Virus Containing the gp50:63 Coding Region gp50:63 expression was examined by immunoprecipitation of $^{14}$C-glucosamine radiolabeled Vgp50:63 infected ST cell extracts with mouse antibody to infectious Vgp50:63 cell extracts. SDS-PAGE analysis of the immunoprecipitates revealed a diffuse band ranging from a molecular weight of 62 Kd to a molecular weight of 58 Kd. No proteins were detected following immunoprecipitation of vaccinia virus infected cells. Analysis of the immunoprecipitates from PRV infected cells showed an identical band pattern to that of Vgp50:63 infected cells. Thus, the gp50:63 synthesized by the recombinant virus infected cells appears very similar to that synthesized by PRV infected cells.

EXAMPLE 5:

Preparation of Vaccine

I. Inactivation of Vaccinia Infected Cells

To make a solution of binary ethyl imine (BEI), 0.8 gm of sodium hydroxide pellets were added to 100 ml of deionized water and incubated 30 minutes at 37° C. 2-bromoethylamine (BEA), 2.05 g, was added and the solution was incubated at 37° C. for an additional hour.

The BEI solution was added to infected virus tissue culture and fluids to a final concentration of 1%. At various times, samples were drawn and inoculated onto monolayers of ST or CV-1 cells to look for cytopathic effects. Normally 96 hours at 37° C. was sufficient to inactivate virus preparations. The extracts were routinely inactivated 120 hours and tested in three back passages on CV-1 monolayers with indirect immunofluorescence assays (Vogt, in *Fundamental Techniques in Virology*, p. 316(1969)) to ensure inactivation had been accomplished.

II. Immunization and Challenge Protocols

Specific pathogenic free (SPF) pigs were purchased and held in isolation until serology had been performed to determine if previous exposure to virus had occurred. After the quarantine the pigs were vaccinated with 2 ml of a vaccine preparation containing 1 ml of BEI inactivated recombinant (gp50:63) divalent vaccinia cell extracts plus 1 ml of 10% lecithin mineral oil. Pigs (between 10-15 lb.) were inoculated intramuscularly (IM) in the neck and challenged by inoculating 0.5 ml of virulent pseudorabies virus in each nostril. The challenge virus was Funkhauser (IND-F2208) pseudorabies virus and the titer was between $10^3$ and $10^5$ TCID$_{50}$ depending on the weight of the pig.

Pigs given combination bacterins were prepared by adding 2 ml of above preparations to a bacterin preparation. The bacterin preparation was prepared as follows:

Seven bacteria strains are desired for a broad protection in pigs. The bacterin can be prepared from the two strains of *Pasteurella multocida* type A and D, three strains of *Hemophilus pleuropneomoniae* (strain 1,5,7), *Bordetella brochiseptica*, and *Erysipelothrix rhusiopathiae*. *E. rhusiopathiae* was grown to an O.D. of 5-6 in media containing 920 ml of basic medium, 30 ml of filtered 50% dextrose, and 50 ml of sterile horse serum. The culture was inactivated by adding formaldehyde to 0.34-0.45% final concentration and merthiolate to a final concentration of 0.01%. Sterile aluminum hydroxide gel (2%) was added to a 25% (v/v) solution. Pasteurella and Bordetella were grown, inactivated and adjuvanted in a similar manner. The Hemophilus strains were grown in a similar manner except gluteraldehyde (0.1%) was used to inactivate and 5% Drakeol TM (Penreco, Butler, Pa.) was used to adjuvant. The combination vaccine was made by combining the inactivated and adjuvanted bacterin preparations (2 ml) with 1 ml of inactivated recombinant PRV subunit preparation.

Prechallenge serum was collected each week. Postchallenge serum was collected starting 3 days after challenge; blood was collected at day 7 and day 14. Additional post challenge clinical measurements were temperature, weight gain and tonsil swabs to determine the level of virus shedding. Virus shedding was scored as the number of pigs in each vaccination group showing positive cytopathic effects during the clinical observation period. Tonsil swabs were vortexed in one ml of PBS and the entire mixture inoculated onto a 24 well cluster plate containing monolayers of ST cells in 199E media (Gibco Laboratories, Grand Island, N.Y.) containing 1 ml per liter of gentamycin.

III. Virus Neutralization Antibody Titration

Using a 96-well plate, 100 µl heat inactivated swine sera was added to the first row on the left side of the plate. Swine samples on PRV virus neutralization were run in duplicate. 50 µl of 199E media treated with gentamycin (1 ml per liter) was added to the remaining wells. Two-fold serial dilutions were made and 50 µl of PRV virus (Bucharest strain diluted 1:500) in 199E media was added to the wells. The plates were incubated for 1 hour at 37° C. Following incubation, 100 µl of ST cells diluted 1:3 in 5% fetal calf serum was added. The plates were incubated at 37° C. and plaque formation was determined after 3 days.

IV. Subunit Vaccine Preparation (SUVA)

Pseudorabies virus (PRV) (IND-F) strain, for use in the preparation of PRV subunit vaccine (SUVA), was propagated in Norden Laboratories' porcine cell line, NL-ST 1. The growth media used to propagate NL-ST 1 cells is medium 199 (Gibco Cat. #400-1100, Grand Island, N.Y.) with Earles' salts (199E media) supplemented with 5% fetal bovine serum (FBS) and 0.025% lactalbumin hydrolysate (LAH). Maintenance medium is medium 199E without FBS or LAH.

Cultures may be propagated in roller bottles or on microcarriers. The microcarriers may be maintained in microcarrier spinner flasks or fermentors. The volume of growth medium used is 500 ml/850 $cm^2$ roller bottle, 1,000 ml/2200 $cm^2$ roller bottle or 1,000 ml/1.5 g Cytodex 3™ (Pharmaco, Piscataway, N.J.) in microcarrier culture.

Cells for the production of SUVA are grown to 85–90% confluency in growth medium. The growth medium is decanted and seed virus is added to a multiplicity of infection (MOI) of 5. A high MOI is employed to insure single-cycle replication. Roller bottle cultures are then brought up to 1/5th of the original volume of growth medium with maintenance medium (the virus inocula is not decanted) and incubated at 37° C. until 80–90% of the cells in the monolayer are swollen and rounded from viral infection but have not become detached from the cell monolayer. Microcarrier cultures are treated in a similar manner except the cultures are filled to half the original volume of growth medium with maintenance medium.

When 80–90% of the cell monolayer becomes infected, the cultures are harvested by decanting the maintenance medium/virus seed suspension and freezing the cell monolayer at −70° C. The monolayers are thawed and 0.025M Tris-Tricine buffer pH 8.6 is added at a ratio of 3 ml buffer/850 $cm^2$ of cell monolayer. This suspension is maintained at 4° C. and lightly sonicated to disrupt the cells. Triton X-100 nonionic detergent is now added to a final concentration of 1% and the suspension stirred at 4° C. overnight. The suspension is centrifuged at 2,000×g for 30 minutes to remove non-solubilized cell debris and microcarriers, if the SUVA was produced in microcarrier culture. The supernatant is centrifuged at 100,000×g for 1 hour to separate the lipid phase from the aqueous phase and the aqueous phase (crude SUVA) is collected for purification by liquid chromatography.

The crude SUVA is loaded onto a lentil bean lectin column which is then washed with 0.025M Tris-Tricine buffer, pH 8.6, until no protein is eluted, as determined by absorption at 280 nm. Following washing, the specifically bound protein is eluted with 0.3M methyl-D-mannoside in 0.025M Tris-Tricine buffer, pH 8.6. The specifically eluted material is SUVA. The protein concentration is determined, the SUVA is diluted to contain 50 μg/ml and adjuvanted.

EXAMPLE 6:

Preparation of a PRV Diagnostic Kit (ELISA)

I. Monoclonal Antibodies

BALB/c female mice (6 to 8 weeks old) were immunized subcutaneously with 0.2 ml of gradient-purified, heat-inactivated (60° C. for 1 hr.) PRV [Indiana-Funkhauser (IND-F)] strain (50 μg protein) emulsified in Complete Freunds Adjuvant. Mice were boosted four weeks later by intraperitoneal (i.p.) inoculation with live virus (100 μg protein) without adjuvant. Immunized animals were sacrificed three days after the last injection of antigen, and spleen cells were fused with NS1/Ag4 mouse plasmacytoma cells (in *Methods in Enzymology, Hybridoma Technology and Monoclonal Antibodies*, p. 3(1986)).

Hybridomas secreting antibody to PRV glycoproteins were selected by screening culture supernatants by ELISA. Culture supernatants were added to wells of polystyrene microtiter plates which were coated with an optimal concentration of crude virus preparations from IND-F or Bucharest (BUK) strains of PRV. The BUK strain of PRV is Norden's licensed vaccine strain and does not produce the gI glycoprotein (Lumniczi, et al., *J. Virol.* 61:796(1987)). Wells coated with similar preparation fron non-infected cells served as controls. Bound antibody was detected by peroxidase-labelled goat anti-mouse immunoglobulin (γ-chain specific). Hybridomas which produced antibody that reacted with IND-F and showed little or no reaction to BUK or cell controls were expanded for further characterization. Positive hybridomas were cloned twice by limiting dilution. Hybridoma designated 2-1B4 was used for production of ascites and development of the diagnostic ELISA.

Stability of the hybridoma for production of antibody after extended passage in tissue culture was determined by ELISA. Two-fold serial dilutions of culture supernatant or ascites obtained prior to or following production of master seed hybridoma were tested in PRV-IND-F antigen-coated microtiter wells as described previously.

Titer of antibody containing fluids was calculated as the reciprocal of the dilution to give a 0.300 absorbance value ($A_{405}$) after 15 minutes incubation with substrate. Results confirmed the antibody titer of culture supernatant remained essentially the same for as long as 20 passages of the hybridoma. Antibody titer of ascites was nearly identical whether produced from pre-master seed or master seed hybridoma cells.

II. Ascites

Hybridomas obtained from cloning were injected into BALB/c female mice (10-14 weeks old) for production of ascites. Mice were treated with 0.5 ml pristane, i.p., seven to ten days prior to i.p. inoculation with $1 \times 10^6$ hybridoma cells in saline. Ascites were collected 10-12 days after injection of hybridoma cells. Cells were removed by centrifugation at $2,500 \times g$ for 30 minutes and the fluid was frozen in aliquots at $-70°$ C.

III. ELISA Diagnostic Kit using Monoclonal Antibody

Recombinant gI protein can be used as a primary antigen in place of whole virus for a competitive ELISA diagnostic kit. The diagnostic gI competitive ELISA test is performed by coating the wells of a polystyrene microtiter plate with an optimal concentration from 400 μg to 600 μg, preferably 500 μg of virus antigen preparation for PRV IND-F strain.

Wells were coated with 100 μl of whole virus antigen diluted in carbonate-bicarbonate buffer pH 9.6 (1.59 g $Na_2CO_3$, 2.93 g $NaHCO_3$/liter deionized $H_2O$). Plates were incubated at 4° C. for 18 hours prior to use. Antigen-coated plates were washed three times with phosphate buffered saline containing 0.05% Tween 20 (PBS-Tw). All subsequent wash steps were performed in this manner. Remaining binding sites were blocked by the addition of 250 μl PBS-1% bovine serum albumin (PBS-BSA) to each well and plates were incubated at 37° C. for 30 minutes. Plates were washed three times and 50 μl aliquots of swine serum were added to wells. After incubation at 37° C. for 1 hour, plates were washed and 50 μl aliquots of an optimal dilution of monoclonal antibody (Mab) in PBS-BSA were added to the wells. Plates were incubated at 37° C. for 1 hour. Bound Mab in washed plates was detected by the addition of 50 μl of peroxidase-labelled goat, anti-mouse immunoglobulin (γ-chain specific) diluted in PBS-BSA. Following incubation at 37° C. for 1 hour, plates were washed and 100 μl ABTS (2.2'-azino-di[3-ethyl-benzthiazoline sulfonate(6)]; Kirkguard and Perry Laboratories, Gaithersburg, Md.) substrate added to wells. Absorbance values ($A_{405}$) were determined after 10-15 minute incubation with substrate at room temperature.

IV. GI Gene Probe Isolation

Recombinant DNA clones representing the $U_s$ region of IND-F genomic DNA are used as a source for diagnostic gene probes. The regions used for gene probes include the DNA encoded between the DraI-Bam HI site as indicated in FIG. 1. The DraI-Bam HI site will identify the major coding body for gI protein. A second probe representing a Bam HI-Sal I site act as a secondary probe for the termination region of the gI mRNA (FIG. 1). Both gene fragments are necessary to determine if the coding region used to make the gI mRNA transcript is present in genomic DNA. Radiolabeled Dra HI-Bam HI or Bam HI to Sal I can be hybridized to pseudorabies Bam HI digested genomic DNA to confirm the absence or presence of the gI mRNA region. Techniques for gene probe synthesis and analysis can be performed as described previously (Maniatis et al., supra, (1982)).

The diagnostic test for gI gene deletion is performed by extracting whole virus DNA from the PRV followed by isolating and digesting 1-2 μgm of whole virus genomic DNA with BamHI. The fragmented DNA is resolved on a 1% agarose gel, denatured and transferred to nitrocellulose using standard laboratory methods. The genomic DNA is then probed with enzyme or radioisotope labeled DNA representing selected regions of the PRV $U_s$ DNA (FIG. 1). Individual DNA bands, for example, specific for the DraI-BamHI DNA (gI) can be detected upon exposure to X-ray film.

EXAMPLE 7:

Preparation of Combination Vaccine

Culture used for production of bacterins are grown to an optical density (OD) of 1-3 units and then inactivated by adding beta propiolactone (BPL) to a final concentration of 0.2%. The cultures are then agitated 12 hours at 20° C. and fixed with formalin (final concentration of 0.4% for Bordetella, Pasteurella, Erysipelatrix and 0.1% gluteraldehyde for Haemophilus). The volume needed for an effective immunizing dose is withdrawn from each and combined in one batch. Normally, the combined inactivated preparation is 2-4 ml total. To adjuvant the preparations, the preparations are placed in an emulsifier (Ross Emulsifier, Long Island, N.Y.) and mineral oil (Penreco, Bulter, Pa.) with lecithin (MRKS Marketing Service, Omaha, Nebr.) (or other desired adjuvant) is added to 5%. The bacterin is agitated or mixed until the preparation is homogenous. Tween 80 ™ (14 ml/L) and Span 80 ™ (6 ml/L) (Sigma Chemical Co., St. Louis, Miss.) can be added to aid in emulsifying the oil phase.

Vaccine recombinant BEI inactivated PRV subunit preparations (see previous examples) can be emulsified alone as described above or placed in combination with the bacterins before emulsifying. Typical combinations containing four or more pathogens are 3-5 ml/dose after adjuvanting where 0.1-1 ml/dose is representative of each individual pathogen preparation.

EXAMPLE 8:

Fusion of Transmissible Gastroenteritis Recombinant DNA Genes to Pseudorabies gp50:gp63 Genes Genes from transmissible gastroenteritis (TGE) virus can be fused to the vaccinia—PRV gp50:gp63 recombinant clones to construct a multivalent vaccine. The TGE glycoprotein E1 or nucleocapsid (N) gene can be recombined to the gp50:63 region at a distance optimum for reinitiation of RNA polymnerase. A transcriptional cassette containing a vaccinia 7.5 Kd promoter and the TGE E1 or N genes can be constructed in standard *E. coli* shuttle vectors. The transcriptional cassette can then be transferred upstream or downstream of the existing vaccinia 7.5 Kd promoter PRV gp50:63 region in plasmid pGS20. The multivalent plasmid p50:63:TGE can then be recombined into TK⁻ vaccinia as described in previous examples. The resulting recombinant virus would contain multivalent subunit components for use as an inactivated vaccine against PRV or TGE induced disease in swine.

In a similar manner, other genes from pathogens problematic to swine (swine dysentry, *mycoplasma pneumonia*, porcine parvovirus, swine influenza) could be incorporated into multivalent vaccine using the vaccinia-PRV gp50:63 as the primary vector for production of subunit antigens in tissue culture.

The above description and examples fully disclose the invention including preferred embodiments thereof. Modifications of the methods described that are obvious to those of skill in the art of vaccine production are intended to be within the scope of the following claims.

What is claimed is:

1. A recombinant pseudorabies virus (PRV) vaccine for inducing immunity in a pig against infection by PRV which comprises an effective amount of recombinant PRV divalent subunit antigens, gp50:63, free of PRV virus particles.

2. The vaccine of claim 1 wherein the divalent subunit antigens are produced by expression of a PRV DNA fragment expressing a colinear transcript for the two pseudorabies proteins gp50 and gp63.

3. The vaccine of claim 1 which contains between 1.0 and 100 µg of the recombinant PRV subunit antigen per ml.

4. The vaccine of claim 3 which contains 5 µg of the recombinant PRV subunit antigens per ml.

5. A method for preparing a vaccine against PRV infection comprising expressing the recombinant PRV subunit antigens, gp50:63, in a mammalian cell culture infected with recombinant vaccinia virus transformed with the gp50:63 coding sequence and inactivating the recombinant vaccinia virus-infected cells with a chemical inactivating agent.

6. The method according to claim 5 wherein the chemical inactivation is achieved by treating the recombinant vaccinia virus-infected cells with binary ethylene imine.

7. The method according to claim 5 wherein the recombinant PRV subunit antigens, gp50:63, are formulated into a vaccine by combining the inactivated recombinant vaccinia virus-infected cells with an adjuvant selected from the group consisting of oil-lecithin, Quil A ™, alhydrogel and mineral oil.

8. The method according to claim 7 wherein the subunit antigens are formulated into a vaccine by combining the inactivated recombinant vaccinia virus-infected cells with an oil-lecithin adjuvant.

9. A method of immunization of porcine animals against PRV infection comprising administering by an oral, intranasal, intraperitoneal, subcutaneous or intramuscular route recombinant PRV subunit antigens, gp50:63.

10. The method of claim 9 wherein the recombinant PRV subunit antigens, gp50:63, are expressed in a mammalian cell culture infected with recombinant vaccinia virus transformed with the gp50:63 coding sequence, the cell culture and virus are inactivated and the inactivated cell culture and virus are administered to the animal.

11. A mammalian cell culture infected with recombinant vaccinia virus transformed with the gp50:63 coding sequence wherein the recombinant vaccinia virus and cell culture have been inactivated.

12. A vaccine dosage unit for inducing immunity to infection by PRV which comprises 0.1 to 5.0 ml of a liquid, for intranasal, intramuscular intraperitoneal, subcutaneous or oral administration to an animal, consisting essentially of 1.0 to 100 µg of recombinant PRV subunit antigens, gp50:63 free of PRV particles.

13. A recombinant pseudorabies virus (PRV) vaccine for inducing immunity in a pig against infection by PRV which comprises an effective amount of recombinant PRV divalent subunit antigens, gp50:63, produced by expression of a recombinant DNA molecule comprising the gp50:63 coding sequence free of PRV particles.

14. The vaccine of claim 13 which comprises an inactivated culture of cells which express the gp50:63 coding sequence.

15. The vaccine of claim 14 in which the cells are mammalian cells.

16. The vaccine of claim 15 in which the cells are mammalian cells which are infected with recombinant vaccinia virus transformed with the gp50:63 coding region of PRV, whereby the cells express the gp50:63 coding region.

* * * * *

UNITED STATES PATENT AND TRADEMARK OFFICE
CERTIFICATE OF CORRECTION

PATENT NO. : 5,069,901

DATED : December 3, 1991

INVENTOR(S) : Jones, Mellencamp, Miller

It is certified that error appears in the above-identified patent and that said Letters Patent is hereby corrected as shown below:

Col. 22, delete Claim 11.

Col. 22,
Claim 12 - Delete "12." and insert --11.--.

Col. 22,
Insert Claim 12.  --12. The method of claim 10 wherein the immunized animals are swine.--

Signed and Sealed this

Eleventh Day of May, 1993

Attest:

MICHAEL K. KIRK

Attesting Officer

Acting Commissioner of Patents and Trademarks